United States Patent
Yamaguchi

(12) 
(10) Patent No.: US 6,423,341 B1
(45) Date of Patent: *Jul. 23, 2002

(54) β-LACTAM ANTIBIOTIC-CONTAINING TABLET AND PRODUCTION THEREOF

(75) Inventor: Hisami Yamaguchi, Osaka (JP)

(73) Assignee: Fujisawa Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,295

(22) PCT Filed: Feb. 21, 1997

(86) PCT No.: PCT/JP97/00509

§ 371 (c)(1),
(2), (4) Date: Aug. 26, 1998

(87) PCT Pub. No.: WO97/31639

PCT Pub. Date: Sep. 4, 1997

(30) Foreign Application Priority Data

Feb. 29, 1996 (JP) .............................................. 8-042743
Nov. 29, 1996 (JP) .............................................. 8-320264

(51) Int. Cl.$^7$ ................................................ A61K 9/20
(52) U.S. Cl. ...................... 424/465; 424/464; 514/960; 514/961
(58) Field of Search ................................ 424/464, 465, 424/466; 514/960, 961, 200, 202, 210, 215

(56) References Cited

U.S. PATENT DOCUMENTS

| 4,950,484 | A | * | 8/1990 | Olthoff et al. |
| 5,514,383 | A | * | 5/1996 | Laly et al. |
| 5,747,068 | A | * | 5/1998 | Mendizabal |
| 5,776,926 | A | * | 7/1998 | Bolz et al. |
| 5,861,141 | A | * | 1/1999 | Mendizabal |

FOREIGN PATENT DOCUMENTS

| EP | 0 599 767 A1 | * | 6/1994 |
| FR | 2 669 221 | * | 5/1992 |

* cited by examiner

*Primary Examiner*—Thurman K. Page
*Assistant Examiner*—Brian K. Seidleck
(74) *Attorney, Agent, or Firm*—Oblon, Spivak, McClelland, Maier & Neustadt, P.C.

(57) ABSTRACT

This invention provides β-lactam antibiotic-containing tablets capable of being orally taken either as such owing to their being small-sized, hence still easily swallowable, or, in the case of administration to the aged encountering some difficulty in swallowing, in the form of dispersions resulting from easy self-disintegration upon being dropped into water in a glass as well as a method of producing the same. The tablets of this invention comprise, on the per-tablet basis, 60–85% by weight of a β-lactam antibiotic, 1–10% by weight of low-substituted hydroxypropylcellulose and/or crosslinked polyvinylpyrrolidone as a disintegrator, and 0.5–2% by weight of a binder. Granules to be compressed for tableting are prepared using water or an aqueous solution of ethanol or the like.

10 Claims, No Drawings

β-LACTAM ANTIBIOTIC-CONTAINING TABLET AND PRODUCTION THEREOF

This application is a 371 of PCT/JP97/00509, filed Feb. 21, 1997.

TECHNICAL FIELD

This invention relates to β-lactam antibiotic-containing tablets and a method of producing the same. More particularly, it relates to tablets of the above variety which can be orally taken either as such or, for taking by, for example, the aged who have difficulties in swallowing, as a dispersion available upon dropping the same into water in a glass for self-disintegration, and to a method of producing the same.

BACKGROUND TECHNOLOGY

Particularly in Europe and America, where β-lactam. antibiotics such as cefixime and cefdinir are administered generally in single doses of as great as 200 mg to 400 mg potency, unit dosage forms, whether they are capsules or tablets, have to be considerably large in size. When 400 mg potency capsules are prepared, for instance, the capsule size reaches approximately No. 0, so that not only patients having difficulties in swallowing but also ordinary adult patients become reluctant to take them or get a repulsive sensation in taking them. Such capsules are indeed difficult to take. In the case of tablets, too, 400 mg potency tablets generally weigh 700 to 1,000 mg per tablet and accordingly are large-sized.

The problems encountered in taking such large dosage forms give an unnecessary sensation of oppression to patients on the occasion of taking them. Improvements in their administrability have thus been required.

Therefore, the present inventor attempted to provide a dosage form with improved administrability by reducing the tablet size as much as possible to thereby facilitate the taking of tablets by the recipient and at the same time to provide a dosage form capable of being taken in the form of a dispersion resulting from rapid self-disintegration upon its being simply dropped into water or the like in a glass, for instance, to thereby make said dosage form administrable to persons of advanced age or children having difficulties in swallowing the dosage form as such. The expression "rapid self-disintegration" as used herein means that when the preparation is dropped into a glass containing a liquid such as water, the tablet form spontaneously collapses generally within 3 minutes, preferably within 1 minute, so that said preparation can be orally taken in dispersion form without awaiting long before taking.

It is indeed easy to produce tablets capable of self-disintegrating very rapidly by incorporating an effervescent agent comprising a combination of sodium hydrogen carbonate and tartaric acid, for instance. However, when such tablets are orally taken, they give off bubbles in the oral cavity, so that patients feel a discomfort or an unnecessary sensation of anxiety. For securing a good shelf-life in a humid environment, it is necessary to use a moisture-proof packaging material, which increases the production cost. Therefore, in developing the dosage form which the present invention is intended to provide, it has been a tough problem to find out a formulation enabling very rapid self-disintegration without the aid of any effervescent component.

For producing β-lactam antibiotic-containing tablets which can be easily ingested as they are and be also ingested in the form of a dispersion resulting from self-disintegration thereof, a technology is described in European Patent EP 0281200 B (corresponding Japanese patent application: Kokai Tokkyo Koho S63-301820), which comprises adding 24 to 70% by weight, based on the weight of the β-lactam antibiotic, of microcrystalline cellulose or microfine cellulose as a first disintegrator and 2 to 20% by weight, on the same basis, of low-substituted hydroxypropylcellulose or the like as a second disintegrator.

However, said first disintegrator, which is used in a large amount, increases the tablet size. In addition, the proportion of a binder component for wet granulation is as low as 0 to 0.1% by weight based on the antibiotic, hence is substantially nil. This is because the use of a binder renders tablets extremely poor in self-disintegrating properties. In the process for producing these tablets, in which no binder is used, a special method of insuring an integrity of the artefact is employed which comprises mixing the antibiotic bulk substance with microcrystalline cellulose and kneading the mixture with the aid of water under application of a great deal of force, without using any alcohol. As a result, large lumps are formed inevitably and they are milled in the wet state and then dried, followed by further milling to provide granules for tableting. It is a problem that these steps are very inefficient.

Meanwhile, tablets containing amoxicillin, which is a β-lactam antibiotic, are commercially available under the trade name of Flemoxin Solutab 500 from Brocades Pharma (Netherlands), the patentee to whom said European patent has been granted. Said tablets each contains 500 mg potency (about 570 mg) of amoxicillin and weighs about 970 mg, hence is very large and not entirely suited for oral administration.

Most β-lactam antibiotics are bitter. Therefore, aqueous dispersions prepared from tablets containing them, when orally taken, give a bitter taste, although the tablets, when taken as such, taste not so bitter. For masking the bitter taste, it thus becomes necessary to incorporate a sweetener, preferably a synthetic sweetener which is effective at low addition levels and thus suited for tablet miniaturization. However, when a commercial synthetic sweetener is incorporated, a problem arises, namely the self-disintegrating properties of tablets become poor, since synthetic sweeteners are soluble in water and become viscous and sticky.

DISCLOSURE OF THE INVENTION

In an attempt to develop a method of improving the rate of self-disintegration of tablets and at the same time miniaturizing the same, the present inventor made investigations concerning the disintegrator species to be used, the level of addition thereof, the binder addition level, the synthetic sweetener particle size and the method of incorporating the same, among others and, as a result, the inventor invented β-lactam antibiotic-containing tablets which are small-sized, show good self-disintegrating properties and can be produced by a conventional method.

Furthermore, the inventor found that when granulation is performed using ethanol, isopropyl alcohol or an aqueous solution of ethanol or isopropyl alcohol, tablets showing better dispersibility upon self-disintegration can be obtained.

The β-lactam antibiotic-containing tablets of this invention contain, per tablet, 60 to 85% by weight of an β-lactam antibiotic, 1 to 10% by weight of low-substituted hydroxypropylcellulose and/or crosslinked polyvinylpyrrolidone as a disintegrator, and 0.5 to 2% by weight of a binder.

Preferably, the β-lactam antibiotic-containing tablets of this invention further contain, per tablet, 0.5 to 15% by weight of a synthetic sweetener and/or a granulated synthetic sweetener.

The β-lactam antibiotic-containing tablet production method of this invention is characterized in that the above-specified respective proportions of a β-lactam antibiotic, the disintegrator and a binder, optionally together with one or more excipients, are granulated using ethanol, isopropyl alcohol or an aqueous solution of ethanol or isopropyl alcohol, the granulation product is mixed with the above-specified proportion of a synthetic sweetener and/or a granulated synthetic sweetener, optionally together with one or more other additives, and the resulting mixture is compressed.

The β-lactam antibiotic to be used in the practice of this invention is one capable of producing a beneficial effect upon oral administration and includes, for example, cefixime and cefdinir respectively represented by the structural formulas shown below as well as cefaclor, cefroxadine, cefadroxil, cefaloglycin, cefalexin, cefradine, amoxicillin, ampicillin and the like.

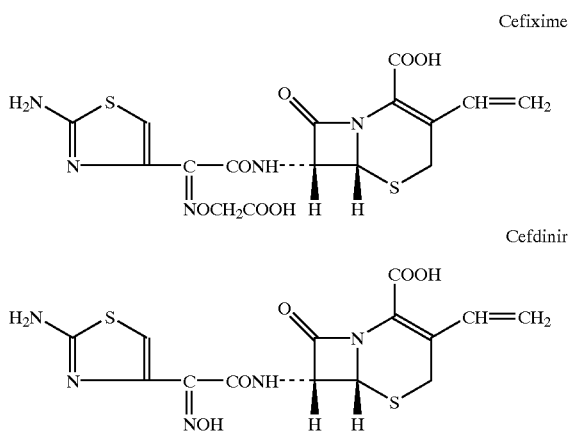

Cefixime

Cefdinir

Each tablet contains such β-lactam antibiotic in a proportion of 60 to 85% by weight, preferably 65 to 80% by weight.

As a result of investigations concerning the disintegrator species to be used in the practice of this invention and the level of addition thereof, it was found that, as compared with such salt type disintegrators as ECG 505 (trademark; carboxymethylcellulose calcium), Ac-Di-Sol (trademark; crosslinked carboxymethylcellulose sodium) and Primojel (trademark; starch glycolic acid sodium), nonion type disintegrators, such as low-substituted hydroxypropylcellulose (L-HPC) and crosslinked polyvinylpyrrolidone, can produce a very good disintegrating effect even when they are added in small proportions. Low-substituted hydroxypropylcellulose is a product derived from cellulose by partial substitution with the 2-hydroxypropoxy group, the degree of substitution being not higher than 25%, preferably 7 to 16%.

Generally, low-substituted hydroxypropylcellulose and crosslinked polyvinylpyrrolidone are incorporated in tablets independently, although both may be used combinedly.

Such disintegrator is used in a proportion of 1 to 10% by weight, preferably 3 to 8% by weight, on a per-tablet basis.

The tablets of this invention further contain binder as an essential constituent. The addition of a binder has an adverse effect on the self-disintegrating properties of tablets, hence is not desirable from the self-disintegration viewpoint. However, the production of tablets without adding any binder give such inconveniences as mentioned hereinbefore.

The inventor of this invention made investigations in search of binder species which would not give adverse effects on the self-disintegrating properties of tablets as well as investigations concerning the addition level thereof. As preferred binders, there may now be mentioned, for example, polyvinylpyrrolidone, hydroxypropylcellulose, preferably low-viscosity type (L-type) hydroxypropylcellulose, hydroxy-propylmethylcellulose, methylcellulose, starch, pregelatinized starch, partly pregelatinized starch, gum arabic, dextrin, pullulan and the like. Among these binders, polyvinylpyrrolidone, hydroxypropylcellulose and hydroxypropylmethylcellulose are more preferred, and polyvinylpyrrolidone is most preferred. When these binders are used in an amount of 0.5 to 2% by weight, preferably 0.8 to 1.5% by weight, on a per-tablet basis, tablets which can self-disintegrate rapidly can be produced by a conventional production method.

Since β-lactam antibiotics, for example cefixime and cefdinir, have a strongly bitter taste, it is necessary to add a synthetic sweetener in cases where tablets are to be taken in the form of dispersions after self-disintegration in water, for instance, though this is not always necessary in cases where tablets are to be taken as such.

As regards the synthetic sweetener addition level, which may vary according to the synthetic sweetener species and the active ingredient β-lactam antibiotic, the sweetener is incorporated in tablets generally in a proportion of 0.5 to 15% by weight, preferably 1 to 10% by weight.

The commercial synthetic sweetener products are generally small, i.e. less than 150 μm, in mean particle size, with particle not smaller than 150 μm accounting for at most 4% of the whole. Incorporation of such products markedly reduces the rate of disintegration of tablets. To improve the disintegration rate, the prior art employs a method which comprises incorporating a large amount of an excipient such as microcrystalline cellulose. However, incorporation of a large amount of such excipient according to said method results in an increase in tablet size, thereby making the tablets difficult to take with ease. The present inventor found that when the particle size of a synthetic sweetener is increased or when a granulated mixture of a synthetic sweetener and light anhydrous silicic acid, hydrated silicon dioxide or the like is added, the rate of disintegration can be improved, namely prevented from retardation.

As a result, an invention was made of miniaturized tablets which can be easily taken as such and, when dropped into water in a glass, can rapidly self-disintegrate, enabling administration thereof in dispersion form.

When such a synthetic sweetener as saccharin, a salt thereof (e.g. saccharin calcium, saccharin sodium), cyclamic acid or a salt thereof (e.g. sodium cyclamate, calcium cyclamate, ammonium cyclamate) is used, said sweetener is required to be not less than 150 μm in mean particle size, preferably not less than 150 μm in particle size. In the case of a sweetener capable of producing a satisfactory bitter-masking effect in small amounts, for example aspartame, it is not always necessary that the mean particle size be not less than 150 μm, since the disintegrability of tablets is little affected.

The synthetic sweetener may be incorporated either in the form of crystalline grains having a mean particle size of not less than 150 μm or in the form of a granulation product meeting the particle size requirement as obtained by wet granulation from the powder-form small in mean particle size or by wet granulation or dry granulation from such powder together with a color additive and/or microcrystalline cellulose or a like excipient.

The granulation product containing light anhydrous silicic acid or hydrated silicon dioxide in addition to a synthetic sweetener can be produced by mixing the synthetic sweetener with 1 to 30% by weight, relative to the synthetic sweetener weight, of light anhydrous silicic acid or hydrated silicon dioxide and granulating the mixture in the conventional manner, if necessary using a binder and/or one or more other additives in common use. It was found that in the case of granulation products containing a synthetic sweetener together with light anhydrous silicic acid or hydrated silicon dioxide, the particle size is not critical, with the result that the self-disintegrating properties are never adversely affected even when the mean particle size is below 150 μm. As regards other ingredients to be used in producing the tablets of this invention, the same ingredients or additives as used conventionally in the production of solid preparations may be mentioned. Thus, in addition to the above-mentioned synthetic sweetener or granulated synthetic sweetener, excipients such as microcrystalline cellulose, lactose, mannitol, starch, etc., flowability improvers such as light anhydrous silicic acid, hydrated silicon dioxide, etc., lubricants such as magnesium stearate, stearic acid, talc, etc., flavoring agents and other agents may be incorporated unless the self-disintegrating properties are adversely affected. When the β-lactam antibiotic has a large particle size, it may be ground prior to use. In this case, however, wet or dry granulation is required to improve the powder flowability in the step of compression.

In a preferred process for producing the tablets of the present invention, the above-specified disintegrator and binder, optionally together with other ingredients, are added to the β-lactam antibiotic, the mixture is granulated by a conventional method, the above-mentioned synthetic sweetener and/or granulated synthetic sweetener, optionally together with one or more other ingredients (e.g. flowability improver, lubricant, flavor), are then further added, and the resulting mixture is subjected to tableting.

When, in the above production process, water is used for granulation in the granulation step, tablets with good self-disintegrating properties are generally obtained. In this connection, the inventor of this invention further found that when ethanol, isopropyl alcohol or a mixture of water and ethanol or isopropyl alcohol is used for granulation, tablets with good self-disintegrating properties and with very good dispersibility upon allowing dispersion in water can be obtained. The concentration of the aqueous solution of ethanol or isopropyl alcohol, which is suited for use, is 3 to 99% (volume/volume), preferably 10 to 60% (volume/volume).

INDUSTRIAL APPLICABILITY

The thus-obtained β-lactam antibiotic-containing tablets of this invention are small in size. For example, a tablet containing 400 mg potency (about 449 mg) of cefixime may weigh not more than 650 mg and a tablet containing 300 mg potency (about 307 mg) of cefdinir not more than 450 mg. They can be orally taken as such with ease. When they are to be taken by the aged, for instance, complaining of some difficulty in swallowing, in an aqueous dispersion form, the tablets can be rapidly disintegrated and dispersed in water. Moreover, the use of ethanol, isopropyl alcohol or an aqueous solution of ethanol or isopropyl alcohol for granulation in the granulation step makes it possible to obtain tablets with still better dispersibility in water.

Test Example 1 (Disintegrator Effect)

According to the formulation shown below in Table 1, cefixime bulk substance, microcrystalline cellulose, one of the disintegrators, light anhydrous silicic acid and magnesium stearate, taken in the respective specified proportions, were mixed up and the mixture was compressed on a single-punch tablet machine to give tablets having a diameter of 11 mm.

The tablets produced by the above method were evaluated for disintegration time in 1,000 ml of water (20±1° C.) using a Japanese Pharmacopeia disintegration tester, but without using any disk, with 30 cycles per minute of basket ascending and descending. The disintegration time data thus obtained are shown in Table 2.

TABLE 1

| Cefixime bulk substance | 448.9 (400 mg potency) |
| Microcrystalline cellulose | 38.9 |
| Disintegrator | 38.9 |
| Light anhydrous silicic acid | 1.2 |
| Magnesium stearate | 5.9 |
| Total | 533.8 mg |

TABLE 2

| Disintegrator | Disintegration time (min.) n = 6 |
| --- | --- |
| Carboxymethylcellulose calcium | 1.2–1.3 |
| Starch glycolic acid sodium | 1.0–1.2 |
| Crosslinked carboxymethylcellulose sodium | 0.8–1.1 |
| Low-substituted hydroxypropylcellulose | 0.3–0.4 |
| Crosslinked polyvinylpyrrolidone | 0.3–0.4 |

As is evident from Table 2, those tablets which contain low-substituted hydroxypropylcellulose or crosslinked polyvinylpyrrolidone in accordance with the present invention disintegrate very rapidly.

Test Example 2 (Binder Study)

According to the formulation shown below in Table.3, cefixime bulk substance micronized by a pin-type mill, microcrystalline cellulose and one of the binders, together with 50% (by volume) ethanol, were granulated in a high speed shear mixer, followed by drying under flowing air at 40° C. for 17 hours and sizing through a 500-μm sieve. The granules sieved out were mixed with low-substituted hydroxypropylcellulose, light anhydrous silicic acid and magnesium stearate, in the respective specified proportions, followed by compression on a single-punch tablet machine, to give tablets each having the specified weight and a diameter of 11 mm.

The tablets produced by the above method were evaluated for disintegration time under the same conditions as in Test Example 1. The disintegration time data thus obtained are shown in Table 4.

TABLE 3

| | |
|---|---|
| Cefixime | 448.9 (400 mg potency) |
| Microcrystalline cellulose | 38.9 |
| Binder | 4.9 (14.6) |
| Low-substituted hydroxypropylcellulose | 38.9 |
| Light anhydrous silicic acid | 1.2 |
| Magnesium stearate | 5.9 |
| Total | 538.7 mg (548.4 mg) |

TABLE 4

| Binder | % addition level (weight in mg) | Disintegration n = 6 |
|---|---|---|
| Polyvinylpyrrolidone | 0.9 (4.9) | 0.6–0.8 |
| Polyvinylpyrrolidone | 2.7 (14.6) | 2.1–2.1 |
| Hydroxypropylcellulose (L type) | 0.9 (4.9) | 1.4–2.0 |
| Hydroxypropylmethylcellulose | 0.9 (4.9) | 1.0–1.5 |

As is evident from Table 4, the tablets produced by using polyvinylpyrrolidone, hydroxypropylcellulose (L type) or hydroxypropylmethylcellulose as the binder disintegrate rapidly.

Test Example 3 (Synthetic Sweetener Particle Size Study)

According to the formulation shown below in Table 5, cefixime bulk substance micronized by a pin-type mill, microcrystalline cellulose, low-substituted hydroxypropylcellulose and polyvinylpyrrolidone, together with 50% (by volume) ethanol, were granulated in a high speed shear mixer, followed by drying under flowing air at 40° C. for 17 hours and sizing using a 500-μm sieve. The granules sieved out were mixed with light anhydrous silicic acid, magnesium stearate, strawberry powder flavor and commercial saccharin calcium, the large particle size saccharin calcium prepared in Example 1 to be mentioned later herein or the granulated mixture of saccharin calcium and light anhydrous silicic acid prepared in Example 2 to be mentioned later herein, in the respective specified proportions, followed by compressing on a single-punch tablet machine to give tablets each having the specified weight and a diameter of 11 mm.

The tablets produced by the above method were evaluated for disintegration time under the same conditions as in Test Example 1. The disintegration time data thus obtained are shown in Table 6.

TABLE 5

| | |
|---|---|
| Cefixime | 448.9 (400 mg potency) |
| Microcrystalline cellulose | 38.9 |
| Low-substituted hydroxypropylcellulose | 38.9 |
| Polyvinylpyrroridone | 4.9 |
| Light anhydrous silicic acid | 1.2 |
| Magnesium stearate | 5.9 |
| Strawberry powder flavor | 7.5 |
| Saccharin calcium or granulated saccharin calcium | 20.0 |
| Total | 566.2 mg |

TABLE 6

| Synthetic sweetner | Mean disintegration time (min.), n = 6 |
|---|---|
| Saccharin calcium (mean particle size < 150 μm) | 3.0 |
| Saccharin calcium (particle size: 150–840 μm) | 0.6 |
| Saccharin calcium-light anhydrous silicic acid mixture granulated (particle size 75–500 μm) | 1.3 |

As is evident from Table 6, the tablets produced by using the saccharin calcium not less than 150 μm in particle size or the granulated mixture of saccharin calcium and light anhydrous silicic acid are positively shorter in disintegration time than the tablets produced by using the commercial saccharin calcium smaller than 150 μm in mean particle size.

Test Example 4 (Influence of the Composition of the Solution for Granulation on the Dispersibility of Tablets)

A 2,200 ml portion of water or an aqueous solution of ethanol was used to granulate a mixture of 4,566 g of cefixime bulk substance micronized by a pin-type mill, 405 g of microcrystalline cellulose, 405 g of low-substituted hydroxypropylcellulose and 50.6 g of polyvinylpyrrolidone in a high speed shear mixer and, after drying under flowing air at 40° C. for 17 hours, the granulation product was sized using a 500-μm sieve. The granules sieved out were mixed with 50.6 g of light anhydrous silicic acid, 101.2 g of magnesium stearate, 75.9 g of strawberry powder flavor and 202.6 g of saccharin calcium (particle size: 150–840 μm), followed by compressing on a rotary tablet machine to give oblong tablets each weighing 579 mg.

The tablets produced by the above method were evaluated, by the method mentioned below, for disintegration time as well as for dispersibility for use in dispersion form.

Disintegration Time

The disintegration time evaluation was made in 1,000 ml of water (20±1° C.) using a Japanese Pharmacopeia disintegration tester, but without using any disk, with 30 cycles per minute of basket ascending and descending.

Dispersibility After Standing of Dispersions Prepared

One tablet was dropped into 20 ml of water placed in a 50-ml beaker and the whole was allowed to stand for 5 minutes for self-disintegration. Then, the beaker was shaken gently for stirring and thereafter allowed to stand for 1 minute, followed by observation of the appearance.

TABLE 7

| | Disintegration time (sec.) | Dispersibility after standing |
|---|---|---|
| Granulation using 50% ethanol | 39 | a |
| Granulation using 10% ethanol | 84 | a |
| Granulation using water | 62 | b |
| Flemoxin Solutab 500 (commercial product) | 46 | b | a: Wholly uniform in color, substantially without any precipitate.
b: A supernatant and a slight amount of a precipitate.

The tablets derived from the granules prepared using ethanol are still better in dispersibility after standing as compared with those derived from the granules prepared using water.

Test Example 5 (Disintegration Test)

Test preparations A: Tablets produced in Example 1 to be mentioned later. B: Tablets produced in Example 7 to be mentioned later. C: Tablets produced in Example 8 to be mentioned later.

Test Method

The disintegration time evaluation was performed in distilled water at 20±1° C. with 4 cycles per minute of basket ascending and descending, using an apparatus prescribed in the Japanese Pharmacopeia (12th edition) under Disintegration Test.

Test Results

A: 1.13 minutes

B: 1.30 minutes

C: 1.02 minutes

The disintegration test results indicate that the test preparations A to C of this invention each shows good disintegrability.

EXAMPLE

Example 1

Water was added to saccharin calcium and the mixture was granulated by a conventional method, followed by drying, sieving and sizing to give saccharin calcium granules not less than 150 μm in particle size.

According to the formulation shown below, micronized cefixime bulk substance, microcrystalline cellulose, low-substituted hydroxypropylcellulose (L-HPC) and polyvinylpyrrolidone were weighed and mixed together, water was then added, and the mixture was granulated. The granulation product was dried under flowing air at 40° C. for 17 hours and then sized using a 500-μm sieve. The granules sieved out were mixed with magnesium stearate, light anhydrous silicic acid, strawberry flavor and the above-mentioned granulated saccharin calcium according to the formulation shown below, followed by compressing on a single-punch tablet machine to give tablets each having the specified weight.

TABLE 8

| | |
|---|---|
| Micronized cefixime bulk substance | 448.9 mg (400 mg potency) |
| Microcrystalline cellulose (Avicel ™ PH101; Asahi Chemical Industry) | 38.9 mg |
| L-HPC (LH-21; Shin-Etsu Chemical) | 38.9 mg |
| Polyvinylpyrrolidone (Kollidon ™ 30; BASF) | 4.9 mg |
| Light anhydrous silicic acid (Aerosil ™; Tomita Seiyaku) | 1.2 mg |
| Magnesium stearate | 5.9 mg |
| Saccharin calcium (not less than 150 μm in particle size) | 20.0 mg |
| Strawberry flavor | 7.5 mg |
| Total | 566.2 mg |

Example 2

Saccharin calcium and light anhydrous silicic acid were mixed together in a ratio of 20:1 and then water was added. The resultant mixture was granulated by a conventional method, followed by drying and sizing to give a granulated mixture of saccharin calcium and light anhydrous silicic acid (75–500 μm in particle size).

Then, tablets were produced following the procedure of Example 1 except that 21 mg of the above granulated mixture was used in lieu of 20 mg of saccharin calcium (Example 1, Table 8).

Example 3

Saccharin calcium and hydrated silicon dioxide were mixed together in a ratio of 20:1 and then water was added. The resultant mixture was granulated by a conventional method, followed by drying and sizing to give a granulated mixture of saccharin calcium and hydrated silicon dioxide (75–500 μm in particle size).

Then, tablets were produced following the procedure of Example 1 except that 21 mg of the above granulated mixture was used in lieu of 20 mg of saccharin calcium (Example 1, Table 8).

Example 4

Tablets each containing 400 mg (potency) of cefixime were produced in the same manner as in Example 1 except that L-HPC of Example 1 (Table 8) was replaced by the same amount of crosslinked polyvinylpyrrolidone (Kollidon™ CL; BASF).

Example 5

Tablets each containing 400 mg (potency) of cefixime were produced in the same manner as in Example 1 except that polyvinylpyrrolidone of Example 1 (Table 8) was replaced by the same amount of hydroxypropylcellulose (HPC-L; Nippon Soda).

Example 6

Tablets each containing 400 mg (potency) of cefixime were produced in the same manner as in Example 1 except that polyvinylpyrrolidone of Example 1 (Table 8) was replaced by the same amount of hydroxypropylmethylcellulose (TC-5R™; Shin-Etsu Chemical).

Example 7

According to the same formulation as that shown in Example 1 (Table 8), micronized cefixime bulk substance, microcrystalline cellulose, L-HPC and polyvinylpyrrolidone were weighed and mixed together, 50% aqueous ethanol was added, and the mixture was granulated. The granulation product was dried under flowing air at 40° C. for 17 hours and then sized using a 500-μm sieve. The granules sieved out were mixed with magnesium stearate, light anhydrous silicic acid, strawberry flavor and the granulated saccharin calcium prepared in Example 1 (not less than 150 μm in particle size) and the resultant mixture was compressed on a single-punch tablet machine to give tablets having the same composition as that in Example 1 (Table 8).

Example 8

According to the formulation shown below, cefdinir-containing tablets were produced in the same manner as in Example 7.

TABLE 9

| | |
|---|---|
| Micronized cefdinir bulk substance | 306.8 mg (300 mg potency) |
| Microcrystalline cellulose (Avicel PH101) | 29.2 mg |
| L-HPC (LH-21) | 29.2 mg |

TABLE 9-continued

| | |
|---|---|
| Polyvinylprrolidone (Kollidon 30) | 3.7 mg |
| Light anhydrous silicic acid (Aerosil) | 0.9 mg |
| Magnesium stearate | 4.4 mg |
| Saccharin calcium (not less than 150 μm in particle size) | 15.0 mg |
| Strawberry flavor | 5.6 mg |
| Total | 394.8 mg |

What is claimed is:

1. A pharmaceutical tablet which can be swallowed whole or rapidly disintegrated in water, comprising at least 300 mg potency and from 60% to 85% by weight of a β-lactam antibiotic, a sweetener, 1 to 10% by weight of hydroxypropylcellulose having a degree of substitution with 2-hydroxypropoxy groups of not higher than 25% and/or crosslinked polyvinylpyrrolidone as a disintegrator and 0.8 to 2% by weight of a binder per tablet, wherein said tablet is made with a granulation product prepared from the β-lactam antibiotic disintegrator, binder and an alcohol selected from the group consisting of ethanol, isopropyl alcohol and aqueous solutions thereof.

2. A tablet as claimed in claim 1, wherein the binder is polyvinylpyrrolidone, hydroxypropylcellulose or hydroxypropylmethylcellulose.

3. A tablet as claimed in claim 1 which further comprises 0.5 to 15% by weight of a synthetic sweetener and/or a granulated synthetic sweetener.

4. A tablet as claimed in claim 3, wherein the synthetic sweetener or the granulated synthetic sweetener has an mean particle size of not less than 150 μm.

5. A tablet as claimed in claim 4, wherein the synthetic sweetener or the granulated synthetic sweetener, is not less than 150 μm in particle size.

6. A tablet as claimed in claim 3, wherein the granulated synthetic sweetener comprises a synthetic sweetener, and light anhydrous silicic acid and/or hydrated silicon dioxide.

7. A tablet as claimed in claim 1, wherein the β-lactam antibiotic is cefixime or cefdinir.

8. A tablet as claimed in claim 7 which contains 400 mg potency of cefixime, the tablet weight being not greater than 650 mg.

9. A tablet as claimed in claim 7 which contains 300 mg potency of cefdinir, the tablet weight being not greater than 450 mg.

10. A method of producing β-lactam antibiotic-containing tablets which comprises admixing a synthetic sweetener and/or a granulated synthetic sweetener, optionally together with one or more other additives, with a granulation product prepared from the β-lactam antibiotic, disintegrator and binder specified in claim 1, optionally together with one or more excipients, by using ethanol, isopropyl alcohol or an aqueous solution of ethanol or isopropyl alcohol, and then tableting the resulting mixture.

* * * * *